(12) United States Patent
Aret

(10) Patent No.: US 8,883,780 B2
(45) Date of Patent: Nov. 11, 2014

(54) CRYSTAL OF A BENZOXAZINONE COMPOUND

(75) Inventor: Edwin Aret, Amsterdam (NL)

(73) Assignee: Norgine B.V., Amsterdam (NL)

(*) Notice: Subject to any disclaimer, the term of this patent is extended or adjusted under 35 U.S.C. 154(b) by 241 days.

(21) Appl. No.: 13/265,599

(22) PCT Filed: Apr. 22, 2010

(86) PCT No.: PCT/JP2010/057110
§ 371 (c)(1),
(2), (4) Date: Dec. 22, 2011

(87) PCT Pub. No.: WO2010/123047
PCT Pub. Date: Oct. 28, 2010

(65) Prior Publication Data
US 2012/0101090 A1  Apr. 26, 2012

(30) Foreign Application Priority Data
Apr. 24, 2009  (JP) ................. 2009-106606

(51) Int. Cl.
*C07D 265/26* (2006.01)
*A61K 31/536* (2006.01)

(52) U.S. Cl.
USPC ........................... 514/230.5; 544/93

(58) Field of Classification Search
USPC ........................ 514/230.5; 544/93
See application file for complete search history.

(56) References Cited

U.S. PATENT DOCUMENTS

| | | | |
|---|---|---|---|
| 6,624,161 B2 * | 9/2003 | Hodson et al. | 514/230.5 |
| 6,656,934 B2 * | 12/2003 | Hodson et al. | 514/230.5 |
| 7,396,952 B2 | 7/2008 | Holzer et al. | |
| 2003/0027821 A1 | 2/2003 | Hodson et al. | |
| 2003/0195206 A1 | 10/2003 | Hodson et al. | |
| 2007/0232825 A1 | 10/2007 | Holzer et al. | |
| 2008/0161301 A1 | 7/2008 | Hodson et al. | |
| 2008/0171891 A1 | 7/2008 | Holzer et al. | |

FOREIGN PATENT DOCUMENTS

| | | |
|---|---|---|
| JP | 2006169244 A | 6/2006 |
| WO | WO-00/40247 A1 | 7/2000 |
| WO | WO 0040247 A1 * | 7/2000 |
| WO | WO 0040569 A1 * | 7/2000 |

OTHER PUBLICATIONS

English Translation of the International Preliminary Report on Patentability for PCT/JP2010/057110 mailed Dec. 1, 2011.
Extended European Search Report for 10767104.2, 6 pages (Sep. 27, 2012).
International Search Report of PCT/JP2010/057110 mailed Jun. 22, 2010.

* cited by examiner

*Primary Examiner* — Kahsay Habte
(74) *Attorney, Agent, or Firm* — Choate, Hall & Stewart, LLP; Charles E. Lyon; John P. Rearick

(57) ABSTRACT

Disclosed is a crystal of 2-(hexadecyloxy)-6-methyl-4H-3,1-benzoxazin-4-one useful as a preventive or therapeutic agent for obesity and the like. Specifically disclosed is a crystal of 2-(hexadecyloxy)-6-methyl-4H-3,1-benzoxazin-4-one having a powder X-ray diffraction pattern in which characteristic peaks appear at powder X-ray diffraction interplanar spacings (d) of around 16.54±0.2, 13.26±0.2, 4.70±0.2, 4.38±0.2, and 3.67±0.2λ.

3 Claims, 1 Drawing Sheet

Fig.1
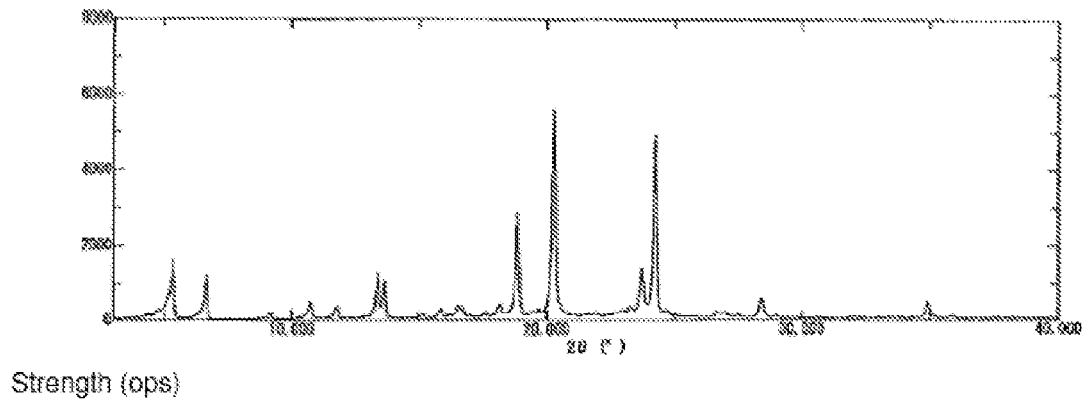
Strength (ops)
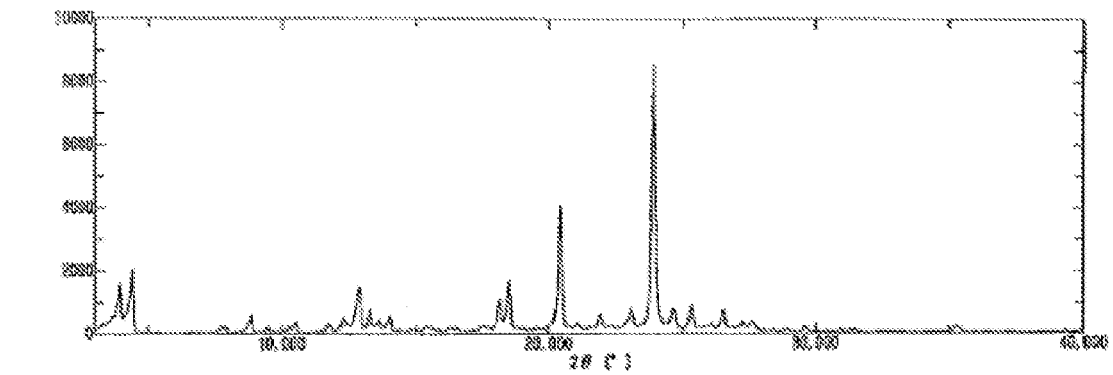
Fig.2
Strength (ops)

US 8,883,780 B2

CRYSTAL OF A BENZOXAZINONE COMPOUND

RELATED APPLICATIONS

This application is a national phase application under 35 U.S.C. 371 of PCT International Application No. PCT/JP2010/057110 (published PCT application no. WO 2010/123047), filed Apr. 22, 2010, which claims priority to Japanese Application No. 2009-106606, filed Apr. 24, 2009, the contents of which are hereby incorporated by reference in their entirety for all purposes.

TECHNICAL FIELD

The present invention relates to a crystal of benzoxazinone compound that is useful in the prevention and treatment of obesity.

BACKGROUND ART

The use of 2-(Hexadecyloxy)-6-methyl-4H-3,1-benzoxazin-4-one having the action of lipase inhibition has been reported as useful in the prevention and treatment of obesity, etc., in the specification of U.S. Pat. No. 6,624,161.

OUTLINE OF THE INVENTION

An agent is needed that is highly effective and safe in the prevention and treatment of obesity. The present invention aims to submit a new crystal of 2-(Hexadecyloxy)-6-methyl-4H-3,1-benzoxazin-4-one that is useful as an agent of prevention and treatment of obesity.

As a result of intensive research, the present inventor succeeded in producing a crystal of 2-(Hexadecyloxy)-6-methyl-4H-3,1-benzoxazin-4-one (Cetilistat) that is extremely safe; discovered that said crystal is pharmaceutically acceptable, and based on this knowledge, completed the present invention.

That is, the present invention relates to;
(1) A crystal of 2-(Hexadecyloxy)-6-methyl-4H-3,1-benzoxazin-4-one with lattice spacing (d) of the powder X-ray diffraction pattern characteristically peaking in the vicinity of 16.54±0.2, 13.26±0.2, 4.70±0.2, 4.38±0.2 and 3.67±0.2, angstroms,
(2) A pharmaceutical containing the crystal of aforementioned (1),
(3) Pharmaceuticals, etc., of aforementioned (2) which are agents for prevention and treatment of obesity.

EFFECTIVENESS OF THE INVENTION

The crystal of the present invention (e.g., hereinafter referred to as A-type crystal and B-type crystal) is useful as a pharmaceutical having exceptional lipase inhibiting action and lipid absorption controlling action, as well as low toxicity.

SIMPLE EXPLANATION OF DIAGRAMS

FIG. 1 shows a powder X-ray diffraction pattern of the B-type crystal of preferred embodiment 1.
FIG. 2 shows a powder X-ray diffraction pattern of the A-type crystal of reference embodiment 1.

DETAILED DESCRIPTION OF THE INVENTION

The crystal 2-(Hexadecyloxy)-6-methyl-4H-3,1-benzoxazin-4-one (or otherwise abbreviated hereinafter to benzoxazinone compound) of the present invention can be a solvate such as a hydrate, etc., or a non-solvate.

The aforementioned hydrate, for example, can be between 0.5 hydrate and 5.0 hydrate. Preferable among these are a 0.5 hydrate, 1.0 hydrate, 1.5 hydrate, 2.0 hydrate and 2.5 hydrate. The 0.5 hydrate, 1.0 hydrate and 1.5 hydrate are particularly advantageous.

The benzoxazinone compound of the present invention or hydrate thereof may also be a deuterium converter.

The benzoxazinone compound crystal of the present invention can also be a solvate other than a hydrate.

Examples of solvate crystal of benzoxazinone compound include alcohol solvate crystals such as methanol solvate crystal and ethanol solvate crystal (preferably $C_{1-6}$ alcohol solvate crystal) and organic solvent hydrate crystal with added water and organic solvent (e.g., alcohol hydrate crystal such as methanol hydrate crystal and ethanol hydrate crystal; preferably $C_{1-6}$ alcohol hydrate crystal).

The crystal of the present invention can be manufactured by crystal transition using either a non-crystal benzoxazinone compound or other crystal benzoxazinone compound.

In crystal transition, the crystal structure undergoes a change above a certain temperature or pressure.

Examples of the 'Crystal Transition Method' include those known in the art, such as crystallization from liquid (e.g., the concentration method, slow-cooling method, reaction method [diffusion method, electrolysis method], hydrothermal cultivation method and fusing method, etc.), crystallization from vapor (vaporization method [sealed tube method, gas flow method], gas phase reaction method, chemical transport method), crystallization from melt [normal freezing method (pull-up method, temperature gradient method, Bridgeman method), zone melting method [zone leveling method, float zone method], special growth method [VLS method, liquid phase epitaxy method]), steam fog method [dissolving crystal in a solvent, and after filtration evaporating the solvent under atmospheric conditions], slurry method [adding crystal to solvent to form a liquid suspension of excess solid, and after agitation at atmospheric temperature or under heating or cooling conditions, filtering of the solid], reduced-pressure drying, grinding, pulverization and pressurization.

Among the aforementioned methods, the slurry method is particularly favorable for obtaining the crystal of the present invention. Particularly advantageous is the method whereby a crystal of benzoxazinone compound is added to a suspension of excess solid in a solvent and, after agitation, the solid is filtered off. Examples of the solvent to use include aromatic hydrocarbons (e.g., benzene, toluene and xylene), hydrocarbon halides (e.g., dichloromethane, chloroform, etc.), saturated hydrocarbons (e.g., hexane, heptane, cyclohexane, etc.), ethers (e.g., diethyl ether, diisopropyl ether, tetrahydroforan, dioxane etc.), nitryls (e.g., acetonitryl, etc.), ketones (e.g., acetone, etc.), sulfoxides (e.g., dimethyl sulfoxide, etc.), acid amides (e.g., N,N-dimethylformamide, etc.), esters (e.g., acetic ether, etc.), alcohols (e.g., methanol, ethanol, isopropyl alcohol, etc.), and water. These solvents can be used alone or two or more can be used in a mixture of suitable ratio (e.g., 1:1 or 1:100). It is advantageous to use aromatic hydrocarbons (e.g., xylene), ethers (e.g., tetrahydrofuran, etc.), and preferably ethers (e.g., tetrahydrofuran, etc.).

The volume of solvent to use is normally approx. 2.5 ml~approx. 10 ml per 1 g of benzoxazinone compound crystal, and preferably approx. 2.5 ml~approx. 3 ml.

After agitating the liquid suspension at atmospheric temperature, it is advisable to cool and agitate again. In the specification of the present invention, room temperature and atmospheric temperature mean approx. 15° C.~approx. 30° C. The period for agitation at atmospheric temperature is normally approx. 2 hours~approx. 24 hours; preferably approx. 15 hours~approx. 24 hours. The period of agitation under cooling is normally approx. 4 hours~approx 24 hours; preferably approx. 16 hours~24 hours. The crystal in the suspension liquid can be separated out by filtration in methods of the known art. Filtration temperature is normally approx. 0° C.~approx. 5° C.

Alternatively, after agitating the liquid suspension at atmospheric temperature, crystallization can take place at atmospheric temperature. The period for agitation at atmospheric temperature is normally approx. 2 hours~approx. 24 hours; preferably approx. 15 hours~approx. 24 hours.

The crystal of the present invention can be obtained by the method of drying to obtain crystal of the known art. Drying can be reduced pressure drying or drying by ventilation. The crystal of the present invention, since it is stable at 25° C.~40° C., is dried at 40° C. or below; preferably at approx. 35° C.~40 C. The drying time is normally approx. 3 hours~24 hours; preferably approx. 15~24 hours.

The non-crystal form of benzoxazinone compound or other crystal of benzoxazinone compound can be manufactured by the method given in U.S. Pat. No. 6,624,161 or other method based on this.

The method of analysis for the obtained crystal is generally the method of crystal analysis by X-ray diffraction. Further, as a method of determining the crystal orientation, the mechanical method or optical method (e.g., FT Raman spectroscopy and solid NMR spectroscopy) can be used.

The peaks in the spectrum obtained from the aforementioned methods of analysis naturally contain constant measuring errors inherent in the method of measurement. The peak values of the spectrum are within the relevant range of error for the crystal of the present invention. For example, the '±0.2' in lattice spacing (d) of the powder X-ray diffraction pattern means within permissible error.

The crystal of 2-(Hexadecyloxy)-6-methyl-4H-3,1-benzoxazin-4-one can be a crystal with a lattice spacing (d) of the powder X-ray diffraction pattern characteristically peaking at 20.07±0.2, 6.86±0.2, 4.79±0.2, 4.34±0.2 and 3.72±0.2, angstroms; preferably with a powder X-ray diffraction lattice spacing (d) characteristically peaking at 22.5±0.2, 20.07±0.2, 9.99±0.2, 7.18±0.2, 6.86±0.2, 4.79±0.2, 4.34±0.2, 3.72±0.2, 3.51±0.2 and 3.36±0.2 angstroms (hereafter referred to as A-type crystal), a crystal with lattice spacing (d) of the powder X-ray diffraction pattern characteristically peaking at 16.54±0.2, 13.26±0.2, 4.70±0.2, 4.38±0.2 and 3.67±0.2, angstroms; preferably with a powder X-ray diffraction lattice spacing (d) characteristically peaking at 16.54±0.2, 13.26±0.2, 8.22±0.2, 6.61±0.2 6.49±0.2, 4.70±0.2, 4.38±0.2, 3.75, 3.67±0.2 and 3.14±0.2 angstroms (hereafter referred to as B-type crystal), A-type crystal or B-type crystal being desirable.

Crystal of 2-(Hexadecyloxy)-6-methyl-4H-3,1-benzoxazin-4-one obtained in this way exhibits excellent lipase inhibiting action and lipid absorption controlling action as well as low toxicity, and is therefore useful as a pharmaceutical. Moreover, since the crystal of the present invention is extremely stable, it is easy to handle and can be manufactured into a solid pharmaceutical constituent with excellent reproducibility.

The crystal of the present invention can be used safely in mammals (e.g., humans, rats, mice, cats, dogs, rabbits, cattle, swine, hamsters, sheep and monkeys) in the prevention and treatment of, for example, obesity, hyperlipidemia (e.g., hypertriglyceridemia, hypercholesterolemia, low HDL and postprandial hyperlipidemia), hyperglycemia (type II diabetes, impaired glucose tolerance), high blood pressure, cardiovascular disease, cerebral stroke, gastrointestinal disease, etc., or complications thereof (e.g., complications of type II diabetes, complications of hyperlipidemia and metabolic syndrome).

The crystal of the present invention has low toxicity, and can be administered safely in unmodified form or in accordance with a method of the known art in a medicinal composition mixed with a pharmacologically acceptable carrier, for example (sugar-coated tablets and film-coated tablets included) powder medicine, granules, capsule medicine (including soft capsules), tablets that dissolve in the mouth, film that dissolves in the mouth, liquid medicine, injection, suppository, slow release medicine, adhesive patch, etc., either orally or non-orally (locally, rectally, intravenously).

The amount of crystal of the present invention administered in a medicinal composition is between approximately 0.01 and 100% by weight of the whole composition. The amount administered varies with the object of treatment, administering route, the patient, etc; for example, when administered orally as a lipase inhibitor in adult patients (body weight: 60 kg) suffering from obesity and/or its complications (e.g., complications of type II diabetes, obesity with complications of hyperlipidemia), the prescribed amount is approximately 1~500 mg per day, preferably approximately 5~250 mg per day, and even more preferably 5~100 mg per day. The crystal of the present invention can be administered once per day or 2~3 times per day.

The pharmacologically acceptable carrier which can be used in the formulation material in manufacturing the medicinal composition of the present invention can be various, common organic or inorganic carrier substances such as, for example, diluting agents, lubricating agents, binding agents, disintegrating agents, water soluble high polymers; solvent in liquid formulation, solvent aid, suspending agents, isotonizing agents, buffering agents and soothing agents. The usual additives such as anti-corrosion agents, anti-oxidants, coloring agents, sweeteners, acidifiers, foaming agents and fragrances can also be used, according to needs.

Examples of 'diluting agents' include lactose, sucrose, D-mannitol, starch, corn starch, crystalline cellulose, light anhydrous silicate and titanium oxide.

Examples of 'lubricating agents' include magnesium sterate, saccharides-fatty acid, polyethylene glycol, talc and steric acid.

Examples of 'binding agents' include hydroxypropyl cellulose, hydroxypropylmethyl cellulose, crystalline cellulose, alpha-starch, polyvinyl pyrrolidone, gum arabic, gelatin, pullulan and low substituted hydroxypropyl cellulose Examples of 'disintegrating agents' include (1) cross povidone, (2) cross carmellose sodium (FMC Ashahi Chemical Industries) and carmellose sodium (Gotoku Yakuhin Co., Ltd.), known as super-disintegrants, (3) carboxymethyl starch sodium (e.g., Matsutani Chemical (KK)), (4) low substituted hydroxypropyl cellulose (e.g., Shinetsu Chemical (KK)) and (5) corn starches. 'Cross povidone' includes polyvinylpolypyrrolidone (PVPP), including cross-linked polymers having the chemical names 1-Vinyl-2-pyrrolidinone homopolymer, and/or suspension of 1-Ethyl-2-pyrrolidinone homopolymer; practical examples being Colidone CL (BASF Co.), Polyplasdone XL (ISP Co.), Polyplasdone XL-10 (ISP Co.) and Polyplasdone INF (ISP Co.).

Examples of 'water soluble high polymer' include ethanol soluble high polymer (e.g., hydroxypropyl cellulose (hereafter referred to as HPC) and other cellulose derivatives, polyvinylpyrrolidone, etc., ethanol insoluble water soluble high polymer [e.g., hydroxypropylmethyl cellulose (hereafter referred to as HPMC), methyl cellulose, sodium carboxymethyl cellulose and other cellulose derivatives, sodium polyacrylate, polyvinyl alcohol, sodium alginate and guar gum.

Examples of 'solvent' include water for injection, alcohol, propylene glycol, macrogol, sesame oil, corn oil and olive oil.

Examples of 'solubilisers' include polyethylene glycol, propylene glycol, D-mannitol, benzyl benzoate, ethanol, trisaminomethane, cholesterol, triethanolamine, sodium carbonate and sodium citrate.

Examples of 'suspending agents' include stearyl triethanolamine, sodium lauryl sulfate, lauryl amino propionate, lecithin, benzalkonium chloride, benzethonium chloride, glycerine monostearate and other surfactants; for example, polyvinyl alcohol, polyvinyl pyrrolidone, sodium carboxymethyl cellulose, methyl cellulose, hydroxymethyl cellulose, hydroxyethyl cellulose, hydroxypropyl cellulose and other hydrophilic high polymers.

Examples of 'isotonizing agents' include dextrose, D-sorbitol, sodium chloride, glycerine and D-mannitol.

Examples of 'buffer' include phosphates, acetate, carbonate, sodium citrate and other buffer solutions.

An example of 'soothing agent' is benzyl alcohol.

Examples of 'anti-corrosion agents' include paraoxybenzoate esters, chlorobutanol, benzyl alcohol, phenethyl alcohol, dehydroacetate and sorbinate.

Examples of 'anti-oxidant' include sulfite salt, ascorbic acid and alpha copherol.

Examples of 'coloring' include food pigments such as food coloring yellow No. 5, food coloring red No. 2 and food coloring blue No. 2; as well as lake color for food, rouge, etc.

Examples of 'sweetener' include sodium saccharide, dipotassium glycyrrhizanate, asparateme, stebia and somatene.

Examples of 'acidifier' include citrate (anhydrous citrate), tartaric acid and malic acid.

An example of 'foaming agent' is sodium bicarbonate.

Examples of 'fragrance' can either be natural or artificial; for example, lemon, lime, orange, menthol and strawberry.

The crystal of the present invention can be manufactured as an orally administered drug according to methods of the known art: for example, by adding a diluting agent, dissolving agent, binding agent and/or lubricating agent and subjecting to compression molding, followed, if necessary, by application of a coating by the known art with the aim of taste masking, enteric dissolvability or persistence. Examples of 'enteric coating' include cellulose acetate phthalate (CAP), hydroxypropylmethyl cellulose phthalate, hydroxymethyl cellulose acetate succinate, metaacrylate copolymer [e.g., Eudragit L30D-55 (Brand Name: Röhm GmBH), Kollicoat MAE 30 D (Brand Name: BASF), Polyquid PA30 (Brand Name: Sanyo Chemical), etc.], carboxymethylethyl cellulose, cerac and other aqueous enteric high polymer bases; metacrylate copolymer [e.g., Eudragit NE30D (Brand Name), Eudragit RL30D (Brand Name), Eudragit RS30D (Brand Name), etc.,] and other controlled release bases; water soluble high polymer; triethyl citrate, polyethylene glycol, acetylated monogylceride, triacetin, castor oil and other plastic agents, either singly or in a mixture of two or more.

The crystal of the present invention can be manufactured into a solid drug formulation such as tablets based on the method described in WO2006/132440.

The crystal of the present invention can be used together with other medications. Examples of the medicinal substances obtained in combinations of the present invention (hereafter referred to as "combined use drug") are as follows.

(1) Therapeutic Medicaments for Diabetes

Insulin drugs [e.g., animal insulin extracted from the pancreas of cows, pigs, etc; bacteria from the large intestine, yeast, synthetic human insulin produced by genetic engineering; zinc insulin; protamine zinc insulin; insulin fragment or derivative (e.g., INS-1); oral insulin], insulin resistance improving agent (e.g., pioglitazone or salt thereof (preferably hydrochloride), rosiglitazone or salt thereof (preferably maleate), Reglixane, Netoglitazone, FK-614, Rivoglitazone, DRF-2593, Edaglitazone (BM-13.1258), R-1197702, compounds listed in WO01/38325, Tesaglitazar, Ragaglitazar, Muraglitazar, ONO-5816, LM-4156, Metaglidasen, (MBX-102), Naveglitazar (LY-519818), MX-6054, LY-510929, Balaglitazone, T-131 or salt thereof, THR-0921, alpha-glucosidase inhibitor (e.g., Bogribose, Acarbose, Miglitol and Emiglitate), Biguanide (e.g., Phenformin, Metformin and Buformin or salt thereof [e.g., hydrochloride, fumaride, succinate]), insulin secretion promoters (sulphonyl urea [e.g., tolbutamide, glybenclamide, glyclaside, chlorpropamide, tolazamide, acetohexamide, glycolpiramide, glymepiride, glypizide, glybuzol], repaglynide, senaglynide, nateglynide, mitiglynide or calcium salt hydrate thereof), GPR40 agonist, GLP-1 receptor agonist [e.g., GLP-1, GLP-1MR agent, NN-2211, AC-2993 (exendin-4), BIM-51077, Aib (8,35) hGLP-1 (7,37)NH$_2$, CJC-1131], dipeptyl peptidase IV inhibitors (e.g., NVP-DPP-278, PT-100, P32/98, Vildagliptin (LAF-237), P93/01, TS-021, Sitagliptin phosphate (MK-431), Saxagliptin (BMS-47 7118), E-3024, T-6666 (TA-6666), 823093, 825964, 815541), beta-3 agonist (e.g., AJ-9677), amylin agonists (e.g., pramlintide), phosphotyrosine phosphatase inhibitors (e.g., sodium banazonate), gluconeogenesis inhibitors (e.g., glycogen phosphorylase inhibitor, glucose-6 phosphatase inhibitor, glucagon antagonist), SGLT (sodium-glucose cotransporter) inhibitor (e.g., T-1095), 11 beta-HSD1 inhibitor (e.g., BVT-3498), adiponectin or its agonist, IKK inhibitor (e.g., AS-2868), leptin low resistance improving drug, somatostatin receptor agonist (e.g., compounds listed under WO01/25228, WO03/42204, WO98/4491, WO98/45285 and WO99/22735), glycokinase activators (e.g., Ro-28-1675), etc.

(2) Therapeutic Medicaments for Diabetic Complications

Aldose reductase inhibitors (e.g., tolrestat, epalrestat, zenarestat, zopolrestat, fidarestat, minalrestat, ranirestat and CT-112), neurotrophic factors and superchargers (e.g., NGF, NT-3, BDNF, neurotrophin production and secretion promoters listed in WO01/14372 [e.g., 4-(4-Chlorophenyl)-2-(2-methyl-1-imidazoryl)-5-[3-(2-methylphenoxy)propyl]oxazol]), nerve regeneration promoters (e.g., Y-128, VX853, prosaptide), PKC inhibitors (e.g., ruboxistaurin mesylate)), AGE inhibitors (e.g., ALT-945, pimagedine, N-phenacyl diazonium bromide (ALT-766), EXO-226, ALT-711, pyridorin, pyridoxamine), active oxygen scavengers (e.g., dioctate), cerebral vasodilators (e.g., tiapride), somatostatin receptor agonists (e.g., BIM23190), apoptosis signal-regulating kinase-1 (ASK-1) inhibitors, etc.

(3) Antilipemic Drugs

HMG-CoA reductase inhibitors (e.g., Pravastatin, Simvastatin, Lovastatin, Atorvastatin, Fluvastatin, Pitavastatin, Rosvastatin or salts thereof, (e.g., sodium salt, calcium salt), squalene synthase inhibitors (e.g., compounds listed in WO97/10224, e.g., N-[[(3R,5S)-1-(3-Acetoxy-2,2-dimethyl-propyl)-7-chloro-5-(2,3-dimetoxyphenyl)-2-oxo-1,2,3,5-tetrahydro-4,1-benzooxazepin-3-il]acetyl][piperidine-4-acetate], fibrate compounds (e.g., bezafibrate, clofibrate, simfibrate, clinofibrate), ACAT inhibitors (e.g., Avasimibe, Eflucimibe), negative ion exchange resin (e.g., cholestylamine), probukol, nicotinate drugs (e.g., nicomol, niceritol, ethyl icosapentate, vegetable sterols (e.g., soysterol, gamma-oryzanol), etc.

(4) Antihypertensive Drugs

Angiotensin converting enzyme inhibitors (e.g., captopril, enalapril, derapril, lisinopril), angiotensin II antagonists (e.g., losartan, candesartan, cilexetil, eprosartan, balsartan, telmisartan, irbesartan, tansartan, 1-[[2'-(2,5-dihydso-5-oxo-4H-1, 2,4-oxadiazol-3-il)biphenyl-4-il]methyl]-2ethoxy-1H-benzimidazol-7-carboxylate), calcium antagonists (e.g., manidipin, nifedipine, amlodipine, efonidipine, nicaldipine), calcium channel openers (e.g., levcromakalim, L-27152, AL0671, NIP-121), alpha-1 blockers (e.g., prazosin hydrochloride, telazosin hydrochloride, bunazosin hydrochloride), beta blockers (e.g., propranolol hydrochloride, pindrol, atenolol, celiprolol hydrochloride, metoprolol tartrate), alpha 1, beta blockers (e.g., labetalol hydrochloride, calbenzilol, bunitrolol), clonizin, etc.

(5) Anti-Obesity Medication

Central weight-loss drugs (e.g., dexaphenfulamine, phenfulamine, phentermine, sibutramine, amphepramone, dexasofetamine, mazindol, phenylpropanolamine, clobenzorex; MCH receptor antagonists (e.g., SB-568849, SNAP-7941 and compounds listed in W001/82925/878341); neuropeptide Y antagonists (e.g., CP-422935); cannabinoid receptor antagonists (e.g., SR-141716, SR147778); ghrelin antagonists), beta 3 agonists (e.g., AJ-9677), peptide based appetite control drugs (e.g., leptin, CNTF (ciliary neurotrophic factor)), cholecystokinin agonists (e.g., lintitript, FPL-15849), dietary intake control drugs (e.g., P-57), etc.

(6) Diuretics

Xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, hydrochlorothiazide, hydroflumethiazide, benzylhydrochlorothiazide, penfluthiazide, polythiazide, methylclothiazide), aldosterone antagonist preparations (e.g., spironolactone, triamterene), carbonate dehydratase inhibitors (e.g., acetazoramide), chlorbenzenesulfonamide preparations (e.g., chlorthalidone, meflucide, indamide), anzosemide, isosorbide, ethacrinate, piretanide, bumetanide, flosemide, meticrane.

(7) Chemotherapeutic Drugs

Alkylating agents (e.g., cyclophoshamide, ifosfamide), metabolic inhibitors (e.g., methotrexate, 5-fluorouracil or its derivative (e.g., flucilon, neoflucilon), antineoplastic antibiotic substances (e.g., mitomycin, adreamycin), vegetable[3] oil antineoplastic agents (e.g., bincristine, bindecine, taxol), cisplatin, carboplatin, etoposide, etc.

(8) Immunomodifiers

Microorganism or bacterial constituents (e.g., muramyl dipeptide derivative, picibanil), immunoenhancing polysaccharides (e.g., lentinan, sizofiran, clecithin, cytokine obtained from genetic engineering methods (e.g., interferon, interleukin (e.g., IL-1, IL-2, IL-12)), colony stimulating factor (e.g., granulocyte colony stimulating factor, erythropoietin), etc.

(9) Antithrombotic Agents

Heparin (e.g., heparin sodium, heparin calcium, dalteparin sodium)), warfarin (e.g., warfarin potassium), antithrombin agents (e.g., argatroban)), thrombolytic agents (e.g., urokinase, tisokinase, alteplase, nateplase, monteplase, pamiteplase)), antiplatelet agents (e.g., ticlopidine hydrochloride, cilostazol, ethyl icosapentate, beraprost sodium, sarpogrelate hydrochloride), etc.

(10) Cachectic Improvers

Progesterone derivatives (e.g., megesterol acetate), metoclopramide agents, tetrahydrocannabinol agents, lipid metabolism improvers (e.g, eicosapentaenoic acid), growth hormones, IGF-1, alternatively factors inducing cachexia TNF-alpha, LIF IL-6, antagonist for oncostatin M, etc.

(11) Antiinflammatory Agents

Steroids (e.g., dexamethasone), sodium hyaluronate, cyclooxygenase inhibitors, (e.g., indometacin, ketoprofen, loxoprofen, meloxicam, ampiroxicam, celecoxib, rofecoxib), etc.

(12) Miscellaneous

Saccharization inhibitors (e.g., ALT-711), antidepressants (e.g., desipramine, amitriptyline, imipramine, floxetine, paroxetine, doxepine), antiarrhythmic agents[4] (e.g., lamotrigine, carbamazepine), acetylcholine receptor ligands (e.g., ABT-594), endoselin receptor agonists (e.g., ABT-627), monoamine uptake inhibitors (e.g., tramadol), indoleamine uptake inhibitors (e.g., floxetine, paroxetine), opiate painkillers (e.g., morphine), GABA receptor agonists (e.g., gabapentin), GABA uptake inhibitors (e.g., tiagabin), alpha 2 receptor agonists (e.g., clonidine), local painkillers (e.g., capsaicin), antianxiety drugs (e.g., benzodiazepine), phosphodiesterase inhibitors (e.g., sildenafil), dopamine receptor agonists (e.g., apomorphine), dopamine receptor antagonists (e.g., haloperidol), serotonin uptake agonists (e.g., tandospiron citrate, smatriptane), serotonin receptor antagonists (e.g., cyproheptadine, ondansetron), serotonin uptake inhibitors serotonin uptake inhibitors (e.g., fluvoxamine maleate, fluoxetine, paroxetine), sleep-inducing drugs (e.g., triazolam, zorpidem), anticholine drugs, alpha-1 receptor blockers (e.g., tamsolosin), muscle relaxants (e.g., baclofen), drugs for prevention and cure of Alzheimer's disease (e.g., donepezil, revastigmine, garantamine), drugs for treatment of Parkinson's disease (e.g., L-dopa), drugs for prevention and cure of multiple sclerosis (e.g., interferon beta-1a), histamine H1 receptor inhibitors (e.g., promethazine hydrochloride), proton pump inhibitors (e.g., lansoprazole, omeprazole, labeprazole or salt thereof (e.g., sodium salt)), NK-2 receptor antagonists, drugs for treatment of HIV infection (e.g., sakinavil, zidovudine, lamivudine, nevirapine), drugs for treatment of chronic obstructive lung disease (e.g., salmeterol, thiotropium bromide, cyromilast), etc.

Examples of anticholine drugs which can be used include atropin, scopramine, homatropin, tropicamide, cyclopentrate, butylscopramine bromide, propantheline bromide, methyl benactyzium bromide, mepenzolate bromide, flavoxsate, pirensebin, ipratopium bromide, trihexyphenidyl, oxybutynin, propiverine, darifenacin, tolterodine, temiberin, trospium chloride or salt thereof (e.g., atropine sulphate, scopolamine hydrobromide, homatropine hydrobromide, cyclopentolate chloride, flavoxate chloride, pirenzebin chloride, trihexifenidil chloride, oxybutynin chloride and tolterodine tartrate; and of these oxybutynin, propiverine, darifenacin, tolterodine, temiberin, trospium chloride or salt thereof (e.g., oxybutynin chloride, tolterodine tartrate) are preferable. Also, acetylcholine esterase inhibitors (e.g., distiguin), etc., can be used.

Examples of NK-2 receptor antagonists include GR159897, GR149861, SR48968 (saredutant), SR144190, YM35375, YM38336, ZD7944, L-743986, MDL105212A, ZD6021, MDL105172A, SCH205528, SCH62373, R-113281 and other piperidine derivatives; RPR106145 and other perhydroisoindol derivatives; SB-414240 and other kinoline derivatives; ZM-253270 and other pyrrolopyrimidine derivatives; MEN11420 nepadutant), SCH217048, L-659877, PD-147714 (CAM-2291), MEN10376, S16474 and other pseudo peptide derivatives; as well as GR100679, DNK333, GR94800, UK-224671, MEN10376, MEN10627 or salt thereof.

Examples of combined use drugs include insulin preparation, insulin low antibiotic improver (preferably pioglitazone or salt thereof (preferable hydrochloride), alpha-glucosidase inhibitors (preferably boglibose), biguanides (preferably metformin), insulin secretion promoters (preferably sulphonyl urea), michiglinide or calcium hydrate thereof), HMG-Coa reductase inhibitors (preferably simvastatin, atorvastatin) are preferred.

The medicines of the present invention with which the crystal of the present invention is mixed or combined include, (1) a single preparation as a medicinal constituent containing the crystal of the present invention and a combined use drug, (2) a preparation containing either a medicinal constituent including the crystal of the present invention or combined use drug. Hereafter, these are referred to by the general identifier, "combined use agents of the present invention".

A combined use agent of the present invention can be manufactured by the same method as employed for the aforementioned solid preparations of the present invention by mixing crystal of the present invention and the effective constituent of a combined use drug with a carrier, etc., obtained either separately or simultaneously, which is acceptable either as is or chemically.

The daily dosage of combined use agent of the present invention varies with the disease, race of the patient, age, gender and body weight of the patient, mode of administration, type of effective constituent and other factors, though there is no particular limitation in the range within which side effects do not occur. The daily dosage of combined use agent of the present invention, for example, in the case of oral administration, as the total administration amount of crystal of the present invention and combined use drug, normally for mammals is approximately 0.005~100 mg per 1 kg of body weight, preferably approx. 0.05~50 mg, even more preferably approx. 0.2~30 mg; such dosage being divided for administration over 1~3 times per day.

On administration of a combined use agent of the present invention, the crystal of the present invention and combined use drug can be administered simultaneously, although the combined use drug can also be administered first, followed by administration of the crystal of the present invention. When administering with a time difference, said time difference varies with the effective constituent, form of agent and method of administration; for example, when the combined use drug is administered first, the time difference to later administration of the crystal of the present invention should be within 1 minute~3 days, preferably within 10 minutes~1 day, and even more preferably within 15 minutes~1 hour. In an example of administering the combined use drug after administration of the crystal of the present invention, the time difference is within 1 minute~1 day, preferably 10 minutes~6 hours, and even more preferably within 15 minutes~1 hour.

In the combined use agent of the present invention, the content of crystal of the present invention in the entire amount of combined use agent is normally 0.1 weight %~65 weight %, preferably 0.3 weight %~50 weight %, and even more preferably 0.5 weight %~20 weight % approximately.

PREFERRED EMBODIMENTS

The preferred embodiments and reference examples mentioned hereinafter give a more detailed description of the present invention, although the present invention is not limited to these.

In the following preferred embodiments and reference examples, room temperature means approx. 15° C.~approx. 30° C. Measurements are taken using the Rigaku RINT2500V X-ray diffractometer for the powder X-ray diffraction (Cu-Kα wavelength: $\lambda$=1.5418 Å, tube voltage: 40 kV, tube current: 400 mA, estimated number of scans: 16).

Preferred Embodiment 1

Crystal of 2-(Hexadecyloxy)-6-methyl-4H-3,1-benzoxazin-4-one (B-Type Crystal)

The A-type crystal (100 g) obtained by the method cited in reference example 1 is suspended in tetrahydrofuran (250 ml) at room temperature, and agitated at room temperature for 3 hours or more. After agitation, the liquid suspension is cooled to 0~10° C. and is agitated at the same temperature for 4 hours or longer. After agitation, the liquid suspension is cooled to 0~10° C. and the crystal is filtered out at the same temperature to obtain the wet crystal. The crystal is filtered out at the same temperature to obtain wet crystal. The thus obtained wet crystal is subjected to reduced pressure drying at 35~40° C. to obtain the B-type crystal (Yield: Approx. 94%). The measuring results of powder X-ray diffraction are given in the following table.

TABLE 1

| Powder X-ray diffraction data (B-type crystal) | | |
|---|---|---|
| 2.θ°) | d value (Å) | Relative strength (%) |
| 5.34 | 16.5355 | 29 |
| 6.66 | 13.2609 | 22 |
| 10.76 | 8.2154 | 9 |
| 13.38 | 6.6120 | 24 |
| 13.64 | 6.4865 | 20 |
| 18.86 | 4.7014 | 52 |
| 20.28 | 4.3753 | 100 |
| 23.72 | 3.7479 | 26 |
| 24.26 | 3.6657 | 89 |
| 28.44 | 3.1357 | 11 |

Preferred Embodiment 2

Crystal of 2-(Hexadecyloxy)-6-methyl-4H-3,1-benzoxazin-4-one (B-Type Crystal)

The A-type crystal (3 g) obtained by the method cited in reference example 1 is suspended in p-xylene (10 ml) at room temperature, and agitated at room temperature for 17 hours or more. After agitation, the crystal is filtered out at the same temperature to obtain wet crystal. The thus obtained wet crystal is subjected to reduced pressure drying at 35~40° C. to obtain the B-type crystal (Yield: Approx. 41%).

Reference Example 1

Crystal of 2-(Hexadecyloxy)-6-methyl-4H-3,1-benzoxazin-4-one (A-Type Crystal)

In accordance with the method contained in Preferred Embodiment 4 of U.S. Pat. No. 6,624,161, raw 2-(Hexadecyloxy)-6-methyl-4H-3,1-benzoxazin-4-one (10 g) is suspended in n-heptane (90 ml), and dissolved with a temperature rise to 50~55 C. After checking that the suspension has dissolved, 0.5 g of active carbon (Hakuro (Registered Trademark) A, Japan Enviro Chemicals, Ltd.) is added, followed by agitation at 50~55 C for 30 min. After agitation, the mixture is filtered while hot, and washed with n-heptane (1 ml). The filtrate and cleaning fluid are cooled to room temperature, and then ethanol drops (40 ml) are added. After adding ethanol, the liquid is cooled to 0~10 C, and agitated at this temperature for 1 hour. After being agitated the crystal is then filtered off and cleaned with ethanol (20 ml) to obtain the wet crystal. The thus obtained wet crystal is subjected to reduced pressure drying at 40~50° C. to obtain the A-type crystal (Yield: Approx. 93%). The measuring results of powder X-ray diffraction are given in the following table.

TABLE 2

Powder X-ray diffraction data (A-type crystal)

| 2.θ(°) | d value (Å) | Relative strength (%) |
|---|---|---|
| 3.92 | 22.5217 | 18 |
| 4.40 | 20.0658 | 24 |
| 8.84 | 9.9949 | 7 |
| 12.32 | 7.1784 | 7 |
| 12.90 | 6.8569 | 18 |
| 18.50 | 4.7920 | 20 |
| 20.44 | 4.3414 | 48 |

TABLE 2-continued

Powder X-ray diffraction data (A-type crystal)

| 2.θ(°) | d value (Å) | Relative strength (%) |
|---|---|---|
| 23.90 | 3.7201 | 100 |
| 25.32 | 3.5146 | 11 |
| 26.52 | 3.3582 | 10 |

The present application is based upon Japan Patent Application 2009-106606 and these details are all included in the present specification.

What is claimed is:

1. A crystal of 2-(Hexadecyloxy)-6-methyl-4H-3,1-benzoxazin-4-one having a powder X-ray diffraction pattern in which characteristic peaks appear at powder X-ray diffraction interplanar spacings (d) of around 16.54±0.2, 13.26±0.2, 4.70±0.2, 4.38±0.2 and 3.67±0.2 angstroms.

2. A solid pharmaceutical composition comprising the crystal of claim 1 and a pharmacologically acceptable carrier.

3. A method for treating obesity comprising administering an effective amount of the pharmaceutical composition of claim 2 to an individual in need thereof.

* * * * *